United States Patent
Camus et al.

(10) Patent No.: US 6,923,768 B2
(45) Date of Patent: Aug. 2, 2005

(54) METHOD AND APPARATUS FOR ACQUIRING AND DISPLAYING A MEDICAL INSTRUMENT INTRODUCED INTO A CAVITY ORGAN OF A PATIENT TO BE EXAMINED OR TREATED

(75) Inventors: Estelle Camus, Erlangen (DE); Hendrik Ditt, Hoechstadt (DE); Reinmar Killmann, Forchheim (DE); Norbert Rahn, Forchheim (DE); Siegfried Wach, Hoechstact (DE)

(73) Assignee: Siemens Aktiengesellschaft, Munich (DE)

( * ) Notice: Subject to any disclaimer, the term of this patent is extended or adjusted under 35 U.S.C. 154(b) by 267 days.

(21) Appl. No.: 10/385,798

(22) Filed: Mar. 11, 2003

(65) Prior Publication Data

US 2003/0220561 A1 Nov. 27, 2003

(30) Foreign Application Priority Data

Mar. 11, 2002 (DE) ......................................... 102 10 648

(51) Int. Cl.$^7$ ................................................ A61B 8/14
(52) U.S. Cl. ...................... 600/463; 600/466; 600/424; 128/916
(58) Field of Search ................................ 600/407–480; 606/130; 345/7–9; 378/162, 205, 207; 128/916

(56) References Cited

U.S. PATENT DOCUMENTS

| 5,016,642 A | | 5/1991 | Dukes et al. |
|---|---|---|---|
| 5,125,410 A | | 6/1992 | Misono et al. |
| 5,257,628 A | * | 11/1993 | Ishiguro et al. ............. 600/463 |
| 5,339,799 A | * | 8/1994 | Kami et al. ................. 600/117 |
| 5,409,000 A | | 4/1995 | Imran |
| 5,662,116 A | * | 9/1997 | Kondo et al. ............... 600/462 |
| 6,126,027 A | | 10/2000 | Thompson |
| 6,533,455 B2 | * | 3/2003 | Graumann et al. ......... 378/205 |
| 6,689,062 B1 | * | 2/2004 | Mesallum ................... 600/439 |
| 6,690,964 B2 | * | 2/2004 | Bieger et al. ............... 600/424 |

FOREIGN PATENT DOCUMENTS

| DE | OS 40 21 102 | 1/1991 |
|---|---|---|
| DE | OS 44 18 868 | 5/1995 |

* cited by examiner

Primary Examiner—Ali Imam
(74) Attorney, Agent, or Firm—Schiff Hardin LLP

(57) ABSTRACT

In a medical treatment/examination device and method for the acquisition and presentation of a medical instrument introduced into a cavity organ of a patient to be examined or treated, particularly in the framework of a cardial examination or treatment with a catheter, intracorporeal registration of 2D ultrasound images of the cavity organ is undertaken using a catheter-like ultrasound acquisition device guided into the cavity organ with simultaneous acquisition of the spatial position and orientation of a 2D ultrasound image by a position acquisition system, a 3D ultrasound image dataset is generated from the 2D ultrasound image, following introduction of the instrument, the instrument is acquired in a coordinate system registered with the 3D ultrasound image dataset, and a 3D reconstruction image is generated on the basis of the 3D image dataset and is presented at a monitor, containing a positionally exact presentation of the instrument in the 3D reconstruction image.

28 Claims, 1 Drawing Sheet

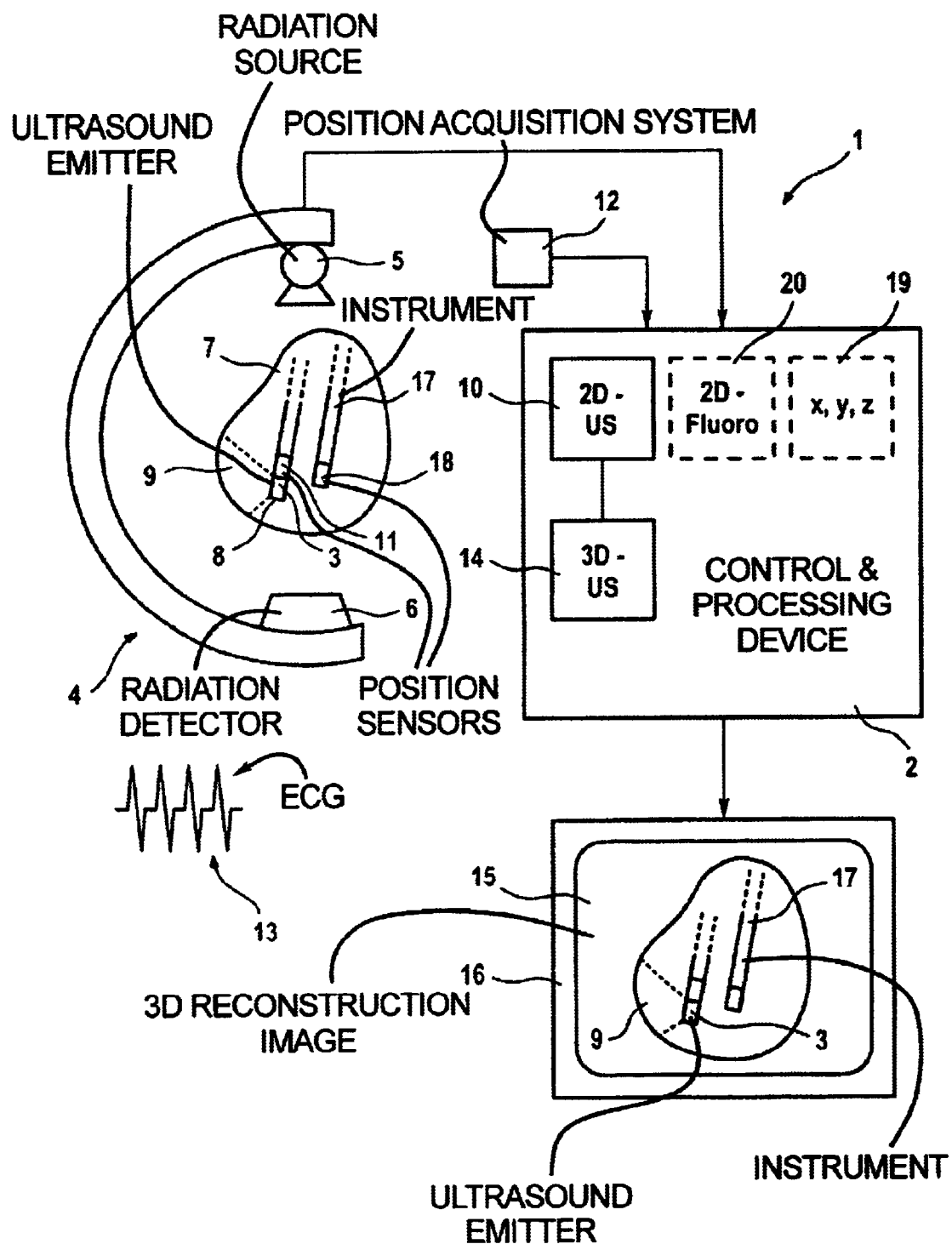

METHOD AND APPARATUS FOR ACQUIRING AND DISPLAYING A MEDICAL INSTRUMENT INTRODUCED INTO A CAVITY ORGAN OF A PATIENT TO BE EXAMINED OR TREATED

BACKGROUND OF THE INVENTION

1. Field of the Invention

The present invention is directed to a method and apparatus for the acquisition and display of a medical instrument that is introduced into a cavity organ of a patient to be examined or treated, particularly in the framework of a cardial examination or treatment with a catheter.

2. Description of the Prior Art

Examinations or treatments of patients are ensuing in minimally invasive procedures to an increasing degree, i.e. with the lowest possible operative outlay. Examples are treatments with endoscopes, laparoscopes or catheters that are respectively introduced into the examination region of the patient via a small body opening. Catheters are frequently utilized in the framework of cardiological examinations, for example in the case of arrhythmias of the heart that are currently treated by ablation procedures.

Under X-ray supervision, i.e. with the acquisition of fluoroscopic images, a catheter is thereby guided into a heart chamber via veins or arteries. In the heart chamber, the tissue causing the arrhythmia is ablated by applying high-frequency current, resulting in the previously arrhythmogenic substrate being left as necrotic tissue. The therapeutic character of this method exhibits great advantages compared to lifelong medication; moreover, this method is also economical in the long view.

A problem associated with such a procedure from a medical/technical point of view is that although the catheter can be visualized very exactly and highly resolved during the X-ray supervision in one or more fluoroscopic images—also called fluoro images—during the intervention, the anatomy of the patient can be imaged only very inadequately in the fluoroscopic images during the intervention. For tracking the catheter, conventionally two 2D fluoroscopic exposures are made from two different projection directions that primarily reside orthogonally relative to one another. On the basis of the visual information of these two exposures, the physician must then determine the position of the catheter on the basis of the physician's own perception, which is often possible only to a relatively imprecise degree.

U.S. Pat. No. 5,409,000 discloses the employment of an ablation catheter with integrated 2D-US (ultrasound) imaging in conjunction with a balloon-like mapping system, wherein the "arms" of the mapping system can be determined by the 2D-US imaging.

German OS 44 18 868 discloses an intravascular ultrasound catheter (IVUS) that is suited only for the US acquisition of vessels since only cross-sectional images of vessels can be generated. Here as well, the 3D reconstruction of the vessel ensues only on the basis of the position of the catheter tip, which is simply moved through the vessel.

U.S. Pat. No. 6,216,027 discloses the localization of catheters whose 3D position is identified with the assistance of ultrasound sensors.

German OS 40 21 102 discloses an apparatus wherein a 2D-US image is combined with a 2D X-ray image in that the US sensor is fixed relative to the X-ray C-arm system with the assistance of an articulated arm (with angle sensors).

U.S. Pat. No. 5,016,642 discloses that slow motion of a beating heart be visualized with the assistance of 2D-US.

U.S. Pat. No. 5,125,410 discloses a purely IVUS vessel application, whereby only 2D-US cross-sectional images of vessels are employed.

SUMMARY OF THE INVENTION

An object of the present invention is to provide a method and an examination or treatment device that facilitates the recognition of the position of the instrument.

This object is achieved in accordance with the invention in a method and device wherein intracorporeal registration of 2D ultrasound images of the cavity organ is undertaken using a catheter-like ultrasound acquisition device guided into the cavity organ with simultaneous acquisition of the spatial position and orientation of a 2D ultrasound image by a position acquisition system, a 3D ultrasound image dataset is generated from the 2D ultrasound image, following introduction of the instrument, the instrument is acquired in a coordinate system registered with the 3D ultrasound image dataset, and a 3D reconstruction image generated on the basis of the 3D image dataset is presented at a monitor with a positionally exact presentation of the instrument in the 3D reconstruction image.

Due to the intracorporeal acquisition of the 2D ultrasound images and the generation of the 3D ultrasound image dataset based thereon, the method and device enable the generation of a three-dimensional inside view of the cavity organ, substantially during the intervention, so the instrument can already be introduced into the cavity during the ultrasound image acquisition or shortly thereafter. When a 3D ultrasound image dataset set has been generated, then the acquisition of the instrument introduced into the cavity organ and the determination of corresponding coordinates follows, the latter, due to their registration with the coordinate system of the 3D ultrasound image dataset, enabling a presentation of the instrument in the 3D reconstruction image at the monitor that is exact as to the instrument's position and orientation. The invention advantageously enables the instrument guidance, i.e., for example, the guidance of a catheter advanced into the heart, to be supported by high-resolution 3D imaging, with the 3D image data being intraoperatively generated, so that the current anatomical conditions are reproduced in the three-dimensional image. Ultrasound is employed as the imaging modality, this enabling the generation of an adequately high-resolution 3D ultrasound image dataset with no radiation load on the patient due to the ultrasound image acquisition. On the basis of the registered instrument acquisition, the positionally exact mixing of the instrument, i.e., for example, the catheter tip or a catheter tip section of a suitably long dimension into the three-dimensional presentation can ensue. Overall, the physician obtains an organ exposure produced quasi in situ with the displayed instrument, which enables a significantly better orientation for the physician in the framework of the subsequent navigation.

The acquisition of the instrument can ensue in various ways. According to a first embodiment of the invention, at least one exposure of a two-dimensional image of the cavity organ showing the instrument can ensue with an image acquisition device for acquiring the instrument, the two-dimensional image being registered with the 3D ultrasound image dataset. The embodiment of the invention is expediently based on the acquisition of at least one 2D fluoroscopic image that is acquired with a suitable X-ray acquisition device. These fluoroscopic or fluoro images usually acquired for catheter monitoring allow an adequately exact acquisition of the instrument. At the same time—for example using a position acquisition system or a marker-less registration arrangement, the registration of the 2D image or images can ensue with the 3D ultrasound dataset coordinate system. Various registration possibilities that can be employed are available to and known by those at the command of a person skilled in the art. A more detailed discussion thereof is not necessary. For common presentation, the two-dimensional image is expediently merged with the 3D ultrasound image dataset or with the 3D reconstruction image. Of course, it is possible to acquire a number of two-dimensional images in sequential succession in order to continuously reproduce and monitor the path of the instrument in the cavity organ. In addition, of course, it is also possible, for example using an X-ray acquisition device that is fashioned as a biplane device, to acquire two 2D fluoroscopic images that preferably reside at an angle of 90° degrees relative to one another in order to identify the position with reference to them, one of them being then superimposed on the 3D ultrasound image dataset.

Another possibility for acquiring the instrument is to employ an instrument having a tip with a position sensor integrated therein, the spatial position thereof being acquired with a position acquisition system in a system-associated coordinate system that is registered with the 3D ultrasound image dataset. Of course, it is possible to employ the same position acquisition system for this purpose with which the positions and orientations of the 2D ultrasound images are also acquired, so the respective coordinates are acquired in the same coordinate system.

If the examination region is a rhythmically or arrhythmically moving region, for example the heart, then for an exact presentation only those 2D ultrasound images that show the cavity organ in the respectively same motion phase can be employed for generating the 3D ultrasound image dataset, and thus the 3D reconstruction image. In order to enable this, in such an instance that an indication of the motion phase of the cavity organ is acquired for the 2D ultrasound images, and only those 2D ultrasound images that are acquired in the same motion phase are employed for generating the 3D ultrasound image dataset. This makes it possible to reconstruct the volume image on the basis of isophase images. It is expedient when—in addition to the motion phase—the point in time of the acquisition of the 2D ultrasound images also is acquired, and only those 2D ultrasound images that are also acquired at the same point in time are employed for generating the 3D ultrasound image dataset.

In the image fusion or merging, it is also expedient in the case of a rhythmically or arrhythmically moving cavity organ to also undertake the acquisition of the two-dimensional image in the motion phase for which the 3D ultrasound image dataset was generated. The same is true of the point in time of the determination of the position of the position sensor integrated in the instrument, which should likewise ensue in the same motion phase. When, additionally, the exposure of the 2D ultrasound images is also triggered time-dependently, then it is expedient for the exposure of the two-dimensional image or the determination of the position of the position sensor to likewise ensue at the same point in time at which the 2D ultrasound images employed for generating the 3D ultrasound image dataset were acquired.

In the case of the heart, the acquisition of the motion phase, and possibly of the time ensues using an ECG registered in parallel. The exposures of the 2D ultrasound images and of the at least one two-dimensional image or the sequentially following two-dimensional images are triggered dependent on this ECG, for example the fluoroscopic images or the determination of the position of the position sensor, which likewise ensues in continuous succession for tracking the movement of the instrument.

It also is possible to undertake the 3D reconstruction, i.e. the generation of the 3D ultrasound image dataset, isochronically or with minimally delayed reconstruction for the acquisition of the 2D ultrasound images. Thus the 2D ultrasound images at the current point in time are employed for the reconstruction, and the 3D ultrasound image dataset is presented. Thus, the 3D ultrasound image dataset is initially presented with only very coarse resolution since only relatively few 2D ultrasound images have been acquired at this initial stage. The resolution of the 3D ultrasound image dataset increases continuously with the increasing number of 2D ultrasound images.

In a further embodiment of the invention, during the acquisition of the 2D ultrasound images, a 3D reconstruction image generated on the basis of the essentially isochronically generated 3D ultrasound image dataset is output at the monitor and shows the position of the ultrasound fan output by the ultrasound generating device or the position and orientation of the ultrasound generating device in real time. This mixing makes it possible for the cardiologist to modify the position and orientation of the ultrasound acquisition catheter such that the subsequently acquired 2D ultrasound images contain medically relevant anatomical regions (for example, the target spot of a following ablation and the like). Moreover, the cardiologist thus can perceive the direction in which the catheter-like acquisition device must be navigated in order to complete or, respectively, designationally expand the 2D ultrasound image dataset.

DESCRIPTION OF THE DRAWINGS

The single FIGURE schematically illustrates a medical examination/treatment device constructed and operating in accordance with the invention.

DESCRIPTION OF THE PREFERRED EMBODIMENTS

In the form of a schematic illustration, the drawing shows an inventive medical examination and/or treatment apparatus 1. In the illustrated example, this includes a central control and processing device 2, an ultrasound acquisition device 3 that is fashioned as a catheter-like applicator and that is in communication with the control and processing device 2, as well as a radiation image acquisition device 4 having a radiation source 5 and a radiation detector 6 with which, for example, 2D fluoroscopic images of an examination region in the form of a cavity organ 7 are possible—a heart (shown enlarged) in this case.

2D ultrasound images 10 of the inside of the cavity organ 7 are acquired with the ultrasound acquisition device 3, which has an ultrasound transmitter 8 that emits an ultrasound fan 9. As can be seen, the ultrasound acquisition device 3 is introduced into the cavity organ 7 and can be navigated therein by being displaced and turned. This turning makes it possible to acquire ultrasound images 10 from substantially all sections of the cavity organ 7 that can be covered with the ultrasound fan 9. With a position sensor 11 integrated into the catheter-like ultrasound acquisition device 3 and a position acquisition system 12, the spatial position and orientation of the ultrasound acquisition device 3 can be continuously acquired in the coordinate system of the position acquisition system 12, so that the spatial position and orientation inn the coordinate system associated to the position acquisition system is known for every acquired 2D ultrasound image. An ECG 13 is registered isochronically with the acquisition of the 2D ultrasound images, so that, in addition to the spatial orientation and position of the images, the motion phase of the cavity organ 7—the heart here—during which a 2D ultrasound image was acquired is also known. This is important since a 3D ultrasound image dataset 14 is generated on the basis of the 2D ultrasound images 10. To this end, only those 2D ultrasound images 10 are employed that show the cavity organ 7 in the same motion phase and—when the time is also recorded in addition to the ECG 13—that are also acquired at the same point in time. A 3D ultrasound image dataset 14 is generated on the basis of identical-phase 2D ultrasound images 10. This is possible since, as stated, the spatial position and orientation of each 2D ultrasound image 10 is known. The 3D reconstruction image 15 generated on the basis of this 3D ultrasound image dataset 14 and is displayed at a monitor 16. It is now possible to undertake the generation of the 3D ultrasound image dataset 14 continuously and isochronically with the exposure of the 2D ultrasound images 10, i.e. the 3D ultrasound image dataset grows with an increasingly number of acquired 2D ultrasound images 10. It has relatively low resolution at the start but becomes more highly resolved with an increasing number of 2D ultrasound images.

As the FIGURE also shows, the ultrasound fan 9 is mixed into the 3D reconstruction image 15 at the monitor. This is possible since the spatial position of the ultrasound acquisition device 3 and the position of the ultrasound fan 9 can be continuously acquired via the position acquisition system 12. By this means, it is possible for the physician to perceive exactly where the ultrasound fan scanning the inside wall of the cavity organ 7 is located. Very specific regions of the cavity organ thus can be approached, or specific regions that were not yet adequately covered in view of the compilation of the 3D ultrasound image dataset 14, can be scanned. The display of the ultrasound acquisition device 3 in the 3D reconstruction image 15 is likewise possible on the basis of the exact knowledge of its spatial position on the basis of the acquisition via the position acquisition system.

Since the ultrasound image acquisition does not stress the patient, it is thus possible to undertake a three-dimensional reconstruction presentation of the inside of the cavity organ 7 by means of the 2D ultrasound images 10 and isochronic reconstruction of a 3D ultrasound image dataset 14.

The reconstructed 3D ultrasound image dataset 14 can then be employed for mixing a medical instrument into it, that is employed in the framework of a treatment or an examination of the cavity organ 7 that ensues immediately thereafter in time or isochronically therewith. In the illustrated example, an instrument 17 in the form of a catheter, for example an ablation catheter with which diseased tissue is to be ablated, is inserted into the cavity organ 7. In order to be able to acquire the exact spatial position and orientation of the instrument 17 or its tip—which is important in order to be able to mix its precise position and orientation into the 3D reconstruction image 15—two possibilities are available. First, a position sensor 18 can be integrated in the tip of the instrument, which, for example is acquired with the same position acquisition system 12 as the position sensor 11 of the ultrasound acquisition device 3, i.e., both are acquired in the same coordinate system that coincides with that of the 3D ultrasound image dataset 14. The position acquisition system 12 continuously supplies the coordinates 19 to the control and processing device 2. This is only shown in broken lines since it is one of the two different acquisition possibilities.

Another acquisition possibility is the employment of the radiation image acquisition device 4. With this, it is possible to acquire 2D fluoro images, also referred to as 2D fluoroscopic images, of the cavity organ 7 wherein the instrument 17 is shown. Here, thus, X-ray monitoring is implemented with which the acquisition of position of the instrument 17 ensues continuously by acquiring the 2D fluoro images 20.

In order to also be able to display the position of the instrument or of the instrument tip with exact position and orientation in the 3D reconstruction image, it is necessary that the 2D fluoro images acquired in a coordinate system associated to the radiation image acquisition device be registered with the coordinate system of the 3D ultrasound image dataset 14. All 2D/3D registration methods familiar to those skilled in the art can be employed for this purpose. The various embodiments of these are well known to those skilled in the art and therefore need not be discussed in greater detail herein.

As soon as the two coordinate systems are registered, the positionally exact display can ensue by fusing a 2D fluoro image 20 with the 3D ultrasound image dataset 14.

Just as the generation of the 3D ultrasound image dataset 14 ensued using only 2D ultrasound images 10 acquired at the same phase (isophase images)—which is possible by the acquisition of the ECG 13 ensuing in parallel therewith—it is also necessary that the acquisition of the position data of the position sensor 18 with the position acquisition system 12, as well as the acquisition of the 2D fluoro images, occur in the same motion phase of the cavity organ wherein the cavity organ 7 is ultimately presented in the 3D reconstruction image 15. To this end, the triggering of the acquisition of the position data of the position acquisition system 12 as well as the triggering of the acquisition mode of the radiation image acquisition device 4, and thus the acquisition of the 2D fluoro images 20, ensue dependent on the ECG 13 recorded in parallel therewith. The triggering ensues under the control of the control and processing device 2 that is provided with the corresponding ECG data. It should be noted that, of course, either an acquisition of the spatial information and the orientation via the position acquisition system 12 or a 2D fluoro image acquisition must be employed for the position acquisition. The position acquisition system can be, for example, an electromagnetic position acquisition system. Those skilled in the art are familiar with such position acquisition systems and require no more detailed description in terms of their exact functioning.

As shown in the FIGURE, the ultrasound acquisition device 3 as well as the medical instrument 17 are located in the cavity organ in the illustrated exemplary embodiment. It is of course also possible to first introduce only the ultrasound acquisition device 3 and to acquire the 2D ultrasound acquisition images 10, and thus the 3D ultrasound image dataset 14, and to undertake the intervention of the actual medical instrument (for example, an ablation catheter) serving for the treatment only after the images and dataset have been generated.

Although modifications and changes may be suggested by those skilled in the art, it is the intention of the inventors to embody within the patent warranted hereon all changes and modifications as reasonably and properly come within the scope of their contribution to the art.

We claim as our invention:

1. A method for acquiring and presenting a representation of a medical instrument that is introduced into a cavity organ of a patient, comprising the steps of:

intracorporeally registering a plurality of 2D ultrasound images of a cavity organ using a catheter-like ultrasound image acquisition device guided into the cavity organ, and simultaneously acquiring a spatial position and orientation of each of said 2D ultrasound images using a position acquisition system;

generating a 3D ultrasound image dataset from said plurality of 2D ultrasound images;

following introduction of an instrument into said cavity organ, acquiring said instrument in a coordinate system registered with said 3D ultrasound image dataset; and generating a 3D reconstruction image from said 3D image dataset, and presenting said 3D reconstruction image at a monitor including a positionally exact presentation of said instrument in said 3D reconstruction image.

2. A method as claimed in claim 1 comprising, for acquiring said instrument, obtaining at least one exposure of a two-dimensional image of said cavity organ, showing said instrument, with an image acquisition device, and registering said two-dimensional image with said 3D ultrasound image dataset.

3. A method as claimed in claim 2 comprising merging said two-dimensional image with said 3D image reconstruction image.

4. A method as claimed in claim 1 comprising the additional step of integrating a position sensor at a tip of said instrument, and acquiring a spatial position of said position sensor with a position acquisition system in a coordinate system of said position acquisition system that is registered with said 3D ultrasound image dataset.

5. A method as claimed in claim 1 wherein said cavity organ exhibits movement having a motion phase, and comprising the additional step of acquiring said motion phase in parallel with said plurality of 2D ultrasound images and, for generating said 3D ultrasound image dataset, employing only 2D ultrasound images in said plurality of 2D ultrasound images acquired at a same motion phase.

6. A method as claimed in claim 5 comprising integrating a position sensor at a tip of said instrument and acquiring a spatial position of said position sensor with a position acquisition in a coordinate system of said position acquisition system registered with said 3D ultrasound image dataset, at a same motion phase as said 2D ultrasound images used to generate said 3D ultrasound image dataset.

7. A method as claimed in claim 6 wherein said cavity organ is a heart, and comprising acquiring an ECG of said heart and identifying said motion phase from said ECG.

8. A method as claimed in claim 5 wherein said cavity organ is a heart, and comprising acquiring an ECG of said heart and identifying said motion phase from said ECG.

9. A method as claimed in claim 5 comprising, in addition to acquiring said motion phase, identifying respective points in time at which said 2D ultrasound images in said plurality of ultrasound images are acquired and, for generating said 3D image dataset employing only 2D ultrasound images in said plurality of 2D ultrasound images acquired at a same point in time.

10. A method as claimed in claim 9 comprising integrating a position sensor at a tip of said instrument and acquiring a spatial position of said position sensor with a position acquisition system in a coordinate of said position acquisition system registered with said 3D ultrasound image dataset, at points in time coinciding with said points in time of the 2D ultrasound images employed for generating said 3D ultrasound image dataset.

11. A method as claimed in claim 10 wherein said cavity organ is a heart, and comprising obtaining an ECG of said heart and using said ECG to identify said points in time at which said 2D ultrasound images are acquired and said points in time at which said position of said position sensor is acquired.

12. A method as claimed in claim 1 comprising generating said 3D ultrasound image dataset isochronically with respect to the acquisition of said plurality of 2D ultrasound images.

13. A method as claimed in claim 12 comprising, during acquisition of said plurality of 2D ultrasound images, generating said 3D reconstruction image from the isochronically generated 3D image dataset, and including, in said 3D reconstruction image, an indication of a position of an ultrasound fan emitted by said ultrasound generating device.

14. A method as claimed in claim 12 comprising, during acquisition of said plurality of 2D ultrasound images, generating said 3D reconstruction image from the isochronically generated 3D image dataset, and including, in said 3D reconstruction image, an indication of a position and orientation in real time of said ultrasound generating device.

15. An apparatus for acquiring and presenting a representation of a medical instrument that is introduced into a cavity organ of a patient, comprising:

a catheter-like ultrasound image acquisition device adapted to be guided into a cavity organ for intracorporeally registering a plurality of 2D ultrasound images of the cavity organ;

a position acquisition system for simultaneously acquiring a spatial position and orientation of each of said 2D ultrasound images using a position acquisition system;

an image computer for generating a 3D ultrasound image dataset from said plurality of 2D ultrasound images;

an instrument acquisition system for, following introduction of an instrument into said cavity organ, acquiring said instrument in a coordinate system registered with said 3D ultrasound image dataset; and a monitor connected to said image computer, said image computer generating a 3D reconstruction image from said 3D image dataset, and presenting said 3D reconstruction image at said monitor including a positionally exact presentation of said instrument in said 3D reconstruction image.

16. An apparatus as claimed in claim 15 wherein said instrument acquisition system obtains at least one exposure of a two-dimensional image of said cavity organ, showing said instrument, with an image acquisition device, and registers said two-dimensional image with said 3D ultrasound image dataset.

17. An apparatus as claimed in claim 16 wherein said image computer merges said two-dimensional image with said 3D image reconstruction image.

18. An apparatus as claimed in claim 15 comprising the additional step of a position sensor adapted to be integrated at a tip of said instrument, and wherein said instrument acquisition system acquires a spatial position of said position sensor in a coordinate system of said position acquisition system that is registered with said 3D ultrasound image dataset.

19. An apparatus as claimed in claim 15 wherein said cavity organ exhibits movement having a motion phase, and comprising acquiring said motion phase in parallel with said plurality of 2D ultrasound images and wherein said image computer, for generating said 3D ultrasound image dataset, employs only 2D ultrasound images in said plurality of 2D ultrasound images acquired at a same motion phase.

20. An apparatus as claimed in claim 19 comprising a position sensor adapted to be integrated at a tip of said instrument and wherein said instrument acquisition system acquires a spatial position of said position sensor in a coordinate system of said position acquisition system registered with said 3D ultrasound image dataset, at a same motion phase as said 2D ultrasound images used to generate said 3D ultrasound image dataset.

21. An apparatus as claimed in claim 20 wherein said cavity organ is a heart, and wherein said system for acquiring said motion phase is an ECG system for acquiring an ECG of said heart and identifying said motion phase from said ECG.

22. An apparatus as claimed in claim 19 wherein said cavity organ is a heart, and comprising wherein said system for said motion phase is an ECG system for acquiring an ECG of said heart and identifying said motion phase from said ECG.

23. An apparatus as claimed in claim 19 wherein said system for acquiring said motion phase additionally identifies respective points in time at which said 2D ultrasound images in said plurality of ultrasound images are acquired and wherein said image computer, for generating said 3D image dataset employing only 2D ultrasound images in said plurality of 2D ultrasound images acquired at a same point in time.

24. An apparatus as claimed in claim 23 comprising a position sensor adapted to be integrated at a tip of said instrument and wherein said instrument acquisition system acquires a spatial position of said position sensor in a coordinate of said position acquisition system registered with said 3D ultrasound image dataset, at points in time coinciding with said points in time of the 2D ultrasound images employed for generating said 3D ultrasound image dataset.

25. An apparatus as claimed in claim 24 wherein said cavity organ is a heart, and wherein said system for acquiring said motion phase is an ECG system for comprising obtaining an ECG of said heart and wherein said image computer uses said ECG to identify said points in time at which said 2D ultrasound images are acquired and said points in time at which said position of said position sensor is acquired.

26. An apparatus as claimed in claim 15 wherein said image computer generates said 3D ultrasound image dataset isochronically with respect to the acquisition of said plurality of 2D ultrasound images.

27. An apparatus as claimed in claim 26 wherein said image computer, during acquisition of said plurality of 2D ultrasound images, generates said 3D reconstruction image from the isochronically generated 3D image dataset, and including, in said 3D reconstruction image, an indication of a position of an ultrasound fan emitted by said ultrasound generating device.

28. An apparatus as claimed in claim 26 wherein said image computer, during acquisition of said plurality of 2D ultrasound images, generates said 3D reconstruction image from the isochronically generated 3D image dataset, and includes, in said 3D reconstruction image, an indication of a position and orientation in real time of said ultrasound generating device.

* * * * *